ized Patent [19]

Feichtinger et al.

[11] 4,078,003
[45] Mar. 7, 1978

[54] METHOD FOR THE PREPARATION OF 1,3-DIAMINO-2,2-DIMETHYL PROPANE

[75] Inventors: Hans Feichtinger, Dinslaken; Heinz Aschmann; Hans-Walter Birnkraut, both of Oberhausen; Ludwig Brinkmann, Frankfurt am Main-Schwanheim; Werner Pluta, Andernach, all of Germany

[73] Assignee: Ruhrchemie Aktiengesellschaft, Oberhausen, Germany

[21] Appl. No.: 723,330

[22] Filed: Sep. 14, 1976

Related U.S. Application Data

[63] Continuation of Ser. No. 522,690, Nov. 11, 1974, abandoned.

[30] Foreign Application Priority Data

Nov. 23, 1973 Germany ............................ 2358355

[51] Int. Cl.$^2$ .......................................... C07C 85/06
[52] U.S. Cl. ............................... 260/583 P; 252/458; 260/583 M; 260/585 B
[58] Field of Search ............ 260/585 B, 583 M, 583 P

[56] References Cited

U.S. PATENT DOCUMENTS

| 2,408,171 | 9/1946 | Johnson | 260/583 |
| 3,268,588 | 8/1966 | Horlenko | 260/585 |
| 3,270,059 | 8/1966 | Winderl et al. | 260/583 P |
| 3,347,926 | 10/1967 | Zech | 260/585 B |
| 3,390,184 | 6/1968 | Moss et al. | 260/585 |
| 3,520,933 | 7/1970 | Adam et al. | 260/585 B |

Primary Examiner—Arthur P. Demers
Attorney, Agent, or Firm—Bierman & Bierman

[57] ABSTRACT

A method for preparing neopentane diamine is disclosed comprising reacting neopentane glycol with ammonia in the presence of hydrogen and a nickel containing catalyst at elevated temperatures and pressures. Neopentane diamine is useful as an intermediate in the preparation of polyurethanes.

3 Claims, No Drawings

METHOD FOR THE PREPARATION OF 1,3-DIAMINO-2,2-DIMETHYL PROPANE

This application is a continuation of U.S. Application Ser. No. 522,690, filed Nov. 11, 1974, now abandoned; which claims the benefit of the priority of German application P 23 58 355.3, filed Nov. 23, 1973.

Neopentane diamine (1,3-diamino-2,2-dimethylpropane) is valuable as an intermediate in the manufacture of polyurethanes; hence a simple process for its production from readily available compounds such as neopentyl glycol is desirable. The present invention is, therefore, directed to an improved process for its preparation.

It is generally known to produce diamines from their corresponding dihydric alcohols. For example, U.S. Pat. No. 3,137,730 teaches reacting ethylene glycol and ammonia (in the presence of a nickel-copper containing catalyst) to obtain ethylene diamine. Similarly, the production of hexamethylene diamine from 1,6 hexanediol, ammonia and hydrogen in the presence of nickel or cobalt containing catalysts is shown in U.S. Pat. No. 3,268,588.

DOS 1,953,263 indicates that glycols can be reacted with ammonia (in the presence of a cobalt, nickel or copper containing catalyst) to form the corresponding amines. DAS 1,172,268 describes the reaction of dihydric aliphatic alcohols with ammonia in the presence of hydrogen. The reaction is carried out using nickel containing catalysts at a temperature of 150° to 300° C under a pressure of at least 10 atmospheres.

However, many dihydric alcohols will not undergo the aforementioned pressure ammonolysis because the bilateral reaction with alpha, omega diols does not proceed via a uniform reaction mechanism. Different reaction products are obtained depending upon the position of the two hydroxyl groups with respect to each other.

As has been found in experiments performed by applicants with nickel catalysts, the diamine can be obtained from propane-1,3-diol only in amounts ranging below 1% because, by beta elimination of a hydroxyl group, allyl alcohol is formed as an intermediate. This alcohol is then primarily reacted to form primary and secondary propylamine. In addition, substantial amounts of hydrocarbons are formed.

In case of neopentylglycol (which is more stable than propane-1,3-diol), dehydration by beta elimination is incapable of taking place. However, hydroxypivaldehyde can be formed by dehydrogenation of a hydroxymethyl group to form the aldehyde. Moreover, cleavage of the resulting aldol to form formaldehyde and isobutyraldehyde would be expected. The resulting fragments would be expected to react with the ammonia and hydrogen present by reducing amination and form methylamine and isobutylamine.

The observations and considerations described above probably account for the fact that the reaction of neopentyl glycol to the corresponding diamine by pressure ammonolysis has not been attempted up to the present. Rather, this diamine has been produced by reacting acetone with nitromethane to form 2,2-dimethyl-1,3-dinitropropane followed by hydrogenation of the dinitro compound (see JACS, 71, p. 3249 (1949)).

It has now been found that the side reactions described above can be largely suppressed in favor of the diamine formation. As a result of the present invention, this compound can be produced directly from neopentyl glycol by means of specific catalysts under particular reaction conditions.

In practicing the present invention, dihydric aliphatic alcohols are reacted with ammonia in the presence of hydrogen and a nickel containing catalyst. The reaction is carried out at a temperature of 150° to 300° C. under pressure of at least 10 atmospheres. More particularly, neopentyl glycol is placed in contact with ammonia and hydrogen under the aforementioned conditions. It has been found preferable to maintain the temperature between 220° and 300° C, most preferably between 240° and 260° C.

Best results have been obtained with a catalyst containing 23 to 60% by weight of nickel, preferably deposited on a support or carrier. Particularly suitable catalysts contain, in addition to nickel, 16 to 40% by weight of chromium. It is best if the chromium is present as $Cr_2O_3$. Kieselguhr is an example of a suitable support. It may contain alumina and magnesia in addition to $SiO_2$.

The molar ratio of hydroxyl groups to ammonia is not critical. A ratio of one hydroxy group to 100 or more moles of ammonia can be used. However, it has been found most advantageous to provide a hydroxy group-ammonia molar ratio of from 1:4 to 1:40, preferably from 1:6 to 1:20.

As a result of the process of the present invention, yields of neopentane diamine in excess of 50% are obtained. The reaction can be carried out, batchwise or continuously with the same good results.

The following examples are intended to illustrate the invention:

EXAMPLE 1

800 grams of neopentyl glycol and 80 g. of a commercial nickel catalyst were introduced into a 10 liter steel autoclave. The catalyst consisted of 55% nickel plus 10 parts by weight of $Al_2O_3$ and 50 parts by weight of kieselguhr per 100 parts by weight of nickel as the carrier material. It is sold by Ruhrchemie AG of Oberhausen-Holton, Germany, under the trade designation 55/10 TS.

The autoclave was heated to 70° C, whereupon 1,600 g. of ammonia were introduced into the steel vessel by means of a pressure pump. Additionally, 20 atmospheres gauge of hydrogen gas were also introduced and the contents of the reaction were brought to 245° C and kept there for four hours, while maintaining vigorous stirring. The vessel stabilized at an operating pressure of 300 atmospheres gauge.

After cooling the reactor and slow venting of the gas phase, the contents of the autoclave were filtered on a Seitz filter. Analysis of the filtrate by gas chromatography showed the following results:

| Products | Percent |
| --- | --- |
| First runnings | 15.7 |
| 1,3-diamino-2,2-dimethylpropane | 71.1 |
| 1-amino-3-hydroxy-2,2-dimethylpropane | 6.2 |
| neopentyl glycol | 5.1 |
| tailings | 1.8 |

Thus, 71.1% of the desired 1,3-diamino-2,2-dimethylpropane (neopentane diamine) was obtained with a conversion of 94.9% based on neopentyl glycol.

By predistillation followed by fine distillation under atmospheric pressure, 548 g. of the diamine were separated from the raw filtrate. The product had a boiling range of from 154° to 156° C. This amount corresponds to 73.7% of the 1,3-diamino-2,2-dimethylpropane to be theoretically expected from neopentyl glycol reacted.

EXAMPLE 2

The reaction described in Example 1 is carried out by using a catalyst consisting of 52% nickel and containing 30 parts by weight of chromium (III) oxide per 100 parts by weight of nickel. Here again, 20 atmospheres gauge of hydrogen gas are forced into the autoclave to activate the catalyst and the reaction is carried out at 250° C for 2 hours.

The raw filtrate is separated from the catalyst and is found to have the following composition:

| Products | Percent |
|---|---|
| First runnings | 11.6 |
| 1,3-diamino-2,2-diemthylpropane | 50.2 |
| 1-amino-3-hydroxy-2,2-dimethylpropane | 21.8 |
| neopentyl glycol | 12.5 |
| tailings | 3.9 |

Thus, an 87.5% conversion, based on neopentyl glycol was obtained with a selectivity of 50.2% of 1,3-diamino-2,2-dimethylpropane. Processing by distillation as described in Example 1 gave 392 g. of the diamine which corresponds to 57% of the theoretical amount to be expected from neopentyl glycol reacted.

EXAMPLE 3

As described in Example 1, 312 g. of neopentyl glycol and 31 g. of the catalyst of Example 2 were introduced into a 10 liter-steel autoclave. Then 1,700 g. of liquid ammonia were pumped into the vessel followed by 20 atmospheres gauge of hydrogen to activate the catalyst. The vessel was then heated for 3 hours at 240° C. After cooling and venting the autoclave, the gas phase was removed and the catalyst was filtered out. Analysis by gas chromatography gave the following composition of the raw filtrate:

| Products | Percent |
|---|---|
| First runnings | 13.1 |
| 1,3-diamino-2,2-dimethylpropane | 80.6 |
| 1-amino-3-hydroxy-2,2-dimethylpropane | 7.6 |
| neopentyl glycol | 1.5 |
| tailings | 0.2 |

Thus, a conversion of 98.5% based on neopentyl glycol was obtained. Processing by predistillation and fine distillation as described in Examples 1 and 2 resulted in 235 g. of diamine. This corresponds to 78% of theoretical.

In order to obtain still further economies, the 1-amino-3-hydroxy-2,2-dimethylpropane produced in the reaction can be recycled and thereby converted into 1,3-diamino-2,2-dimethylpropane in this process.

What is claimed is:

1. A process for the production of 1,3 diamino-2,2 dimethyl propane comprising contacting neopentyl glycol, ammonia and hydrogen at a temperature of 150° – 300° C. and a pressure of at least 10 atmospheres in the presence of a nickel catalyst on a carrier, said catalyst containing 23 to 60% by weight of nickel and 16 to 40% by weight of chromium, and the hydroxyl group to ammonia ratio is 1:6 to 1:20.

2. The process according to claim 1 wherein said temperature is 240° to 260° C.

3. The process according to claim 1 wherein the chromium is in the form of $Cr_2O_3$.

* * * * *